United States Patent
Wadsworth et al.

(10) Patent No.: US 7,935,852 B2
(45) Date of Patent: May 3, 2011

(54) FLUORIDATION METHOD

(75) Inventors: Harry John Wadsworth, Amersham (GB); Peter Anthony Devenish, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 149 days.

(21) Appl. No.: 10/559,878

(22) PCT Filed: Apr. 6, 2005

(86) PCT No.: PCT/GB2005/001344
§ 371 (c)(1),
(2), (4) Date: Dec. 7, 2005

(87) PCT Pub. No.: WO2005/097713
PCT Pub. Date: Oct. 20, 2005

(65) Prior Publication Data
US 2007/0092441 A1    Apr. 26, 2007

(30) Foreign Application Priority Data

Apr. 8, 2004 (GB) .................................. 0407952.1

(51) Int. Cl.
*C07B 59/00* (2006.01)
*C07C 17/20* (2006.01)
*C07C 25/13* (2006.01)
*C07C 45/63* (2006.01)
*C07C 49/807* (2006.01)
*C07C 49/84* (2006.01)

(52) U.S. Cl. ......................... 568/651; 568/661; 568/775

(58) Field of Classification Search .................. 568/775, 568/656, 661
See application file for complete search history.

(56) References Cited

U.S. PATENT DOCUMENTS

2006/0292060 A1* 12/2006 Wadsworth et al. .......... 423/500

FOREIGN PATENT DOCUMENTS

WO        03/002157        1/2003

OTHER PUBLICATIONS

Chen et al. Synlett, 2000, No. 8, 1175-1177.*
J. Chem Soc., Perkin Trans., 1, 2043-9 (1998) A. Shah et.al., "The synthesis of [18F]fluoroarenes from the reaction of cyclotron-produced [18F]fluoride ion with diaryliodonium salts".
GB 0407952.1 Search Report dated Aug. 16, 2004.

* cited by examiner

*Primary Examiner* — Venkataraman Balasubramanian

(57) ABSTRACT

A method for the fluoridation of an iodonium salt with a fluoride ion source which can be carried out in an aqueous reaction solvent.

19 Claims, No Drawings

FLUORIDATION METHOD

This application is a filing under 35 U.S.C. 371 of international application number PCT/GB2005/001344, filed Apr. 6, 2005, which claims priority to application number 0407952.1 filed Apr. 8, 2004, in Great Britain the entire disclosure of which is hereby incorporated by reference.

TECHNICAL FIELD OF THE INVENTION

The present invention relates to the fluoridation of iodonium salts. Specifically, the present invention relates to a method for the fluoridation of iodonium salts wherein the reaction proceeds in the presence of water. The invention is also suitable for carrying out radiofluoridation of iodonium salts. The radiofluoridated compounds obtained by the method of the invention are useful for inclusion in pharmaceutical compositions. Furthermore, the invention relates to a kit for facilitating the performance of the method of the invention.

DESCRIPTION OF RELATED ART

Nucleophilic substitution by fluoride is regarded as one of the most attractive ways for introducing fluorine into an organic compound. In order to increase the reactivity of fluoride and to avoid hydroxylated by-products resulting from the presence of water, water is removed from fluoride prior to the reaction and the fluorination reactions are carried out using anhydrous reaction solvents [Aigbirhio et al 1995 *J. Fluor. Chem.* 70 pp 279-87]. The removal of water from the fluoride ion is referred to as making "naked" fluoride ion. This is regarded in the prior art relating to nucleophilic fluoridation as a step necessary to increase the reactivity of fluoride as well as to avoid hydroxylated by-products resulting from the presence of water [Moughamir et al 1998 *Tett. Letts.* 39 pp 7305-6].

A further step that is used to improve the reactivity of fluoride ion for fluoridation reactions is to add a cationic counterion prior to the removal of water. The counterion should possess sufficient solubility within the anhydrous reaction solvent to maintain the solubility of the fluoride ion. Therefore, counterions that have been used include large but soft metal ions such as rubidium or caesium, potassium complexed with a cryptand such as Kryptofix™, or tetraalkylammonium salts. A preferred counterion for fluoridation reactions is potassium complexed with a cryptand such as Kryptofix™ because of its good solubility in anhydrous solvents and enhanced fluoride reactivity.

[$^{18}$F]-fluoride ion is typically obtained as an aqueous solution which is a product of the irradiation of an [$^{18}$O]-water target. It has been widespread practice to carry out various steps in order to convert [$^{18}$F]-fluoride into a reactive nucleophilic reagent, such that it is suitable for use in nucleophilic radiolabelling reactions. As with non-radioactive fluoridations, these steps include the elimination of water from [$^{18}$F]-fluoride ion and the provision of a suitable counterion [*Handbook of Radiopharmaceuticals* 2003 Welch & Redvanly eds. ch. 6 pp 195-227]. Nucleophilic radiofluorination reactions are then carried out using anhydrous solvents [Aigbirhio et al 1995 *J. Fluor. Chem.* 70, pp 279-87]. A further factor that is important for radiofluoridations as contrasted with non-radioactive fluoridations is time due to the relatively short half life of [$^{18}$F], which is 109.7 minutes.

Preparation of [$^{18}$F]-aryl fluorides has been reported by Pike and Aigbirhio [1995 *J. Chem. Soc. Chem. Comm.* pp 2215-6]. The reported method was an aromatic nucleophilic substitution reaction in which [18]-fluoride Kryptofix™ was reacted with a diaryliodonium salt in acetonitrile. The [18]-fluoride Kryptofix™ was freed from water by heating under a stream of nitrogen. Water free acetonitrile was used in the reaction. The rigorous elimination of water from the reaction was thought necessary for good yields. Shah et al [1998 *J. Chem. Soc., Perkin Trans.* 1, pp 2043-6] examined the radiofluoridation of diaryliodonium salts using dry [$^{18}$F]fluoride in a variety of anhydrous solvents. Of the solvents evaluated (dichloromethane, chloroform, dimethyl sulfoxide, dimethyl formamide, tetrahydrofuran and acetonitrile) the highest yields were obtained when acetonitrile was used, which was also found to be the best solvent for the diaryliodonium salts. A comparison was also made in this study between use of [$^{18}$F]-KF complexed with a cryptand and [$^{18}$F]-CsF and it was found that greater yields were obtained when [$^{18}$F]-KF complexed with a cryptand was used as the radiofluorinating agent.

An alternative approach to the preparation of aryl fluorides was adopted by Van der Puy (1982, *J. Fluorine Chem.*, 21 385-392) who heated an aryl iodonium salt with potassium fluoride in the absence of solvent. The aryl iodonium salt is said to have a non-nucleophilic counter-ion.

SUMMARY OF THE INVENTION

Surprisingly, in contrast to the teachings of the prior art, the present invention demonstrates that the nucleophilic fluorination of iodonium salts can be successfully carried out in the presence of water and that improved yields are obtained compared with reactions carried out using anhydrous conditions. An additional benefit in the context of radiofluoridations is that time is saved if the fluoride drying step is left out, resulting in an improved radiochemical yield. Also Kryptofix™ is no longer required in the reaction to increase the reactivity of the fluoride ion. The invention also provides a pharmaceutical composition comprising compounds obtained by the method of the invention as well as a kit for carrying out the method of the invention.

DETAILED DESCRIPTION OF THE INVENTION

In a first aspect, the present invention relates to a method for the production of an aromatic or hetroaromatic fluorine-labelled compound comprising fluoridation of an iodonium salt with a fluoride ion source characterised in that the reaction solvent comprises water.

Fluoridated product has been obtained when the reaction solvent is 100% water, but the best yields have been obtained when the reaction solvent is a mixture of water and a water-miscible solvent.

In the context of the present invention, a "water-miscible solvent" is any solvent that can be uniformly mixed with water. Examples of suitable water-miscible solvents of the invention are acetonitrile, ethanol, methanol, tetrahydrofuran and dimethylformamide and dimethyl sulphoxide. A preferred water-miscible solvent of the invention is acetonitrile.

Preferably, the volume:volume ratio of water:water-miscible solvent is from 1:99 to 1:1 and most preferably from 10:90 to 30:70.

Most surprisingly, the present inventors have found not only that the reaction proceeds satisfactorily in the presence of water but also that the presence of water in the reaction mixture actually improves the product yield. This has been shown to be the case with a variety of fluoride counter-ions.

In prior art fluoridation reactions carried out under anhydrous conditions, the preferred counter-ion is said to be potassium complexed with Kryptofix™. However, the present inventors have found that with water present in the reaction solvent, potassium can also act as a successful counter-ion in the absence of Kryptofix™. Other metal ions such as caesium and sodium are also suitable counter-ions in the process of the invention.

It is an additional advantage of the process that it is not necessary to provide the counter-ion as a complex as this removes from the process the step of complexing the counter-ion with a complexing agent such as Kryptofix™.

Preferably, the method of the invention comprises the fluoridation of an iodonium salt of Formula (I) or (II):

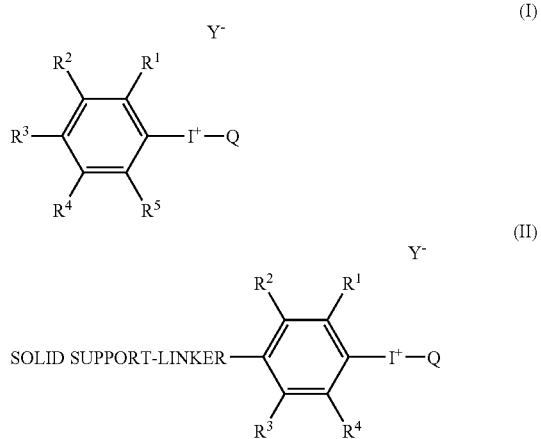

wherein:
Q is an electron deficient aromatic or heteroaromatic moiety;
each of $R^1$, $R^2$, $R^3$, $R^4$ and $R^5$ is independently hydrogen, —O($C_{1-10}$ alkyl) or $C_{1-10}$ alkyl; and
$Y^-$ is a counter ion such as trifluoromethane sulfonate (triflate), perfluoro $C_2$-$C_{10}$ alkyl sulphonate, trifluoroacetate, methane sulfonate (mesylate), toluene sulfonate. (tosylate), tetraphenylborate;
to give a product of general formula (III):

where Q is as defined for general formulae (I) and (II).

In the context of the present specification, the term "$C_1$-$C_{10}$ alkyl" refers to a fully saturated straight or branched hydrocarbon chain having up to 10 carbon atoms. Examples include methyl, ethyl isopropyl, n-butyl, tertiary butyl, n-octyl and n-decyl.

In the context of the present specification, the term "aromatic" refers to a group comprising one or more rings, at least one of which has aromatic character and having from 5 to 14 ring carbon atoms. The rings of the aromatic group may be fused or may be connected via a bond.

The term "heteroaromatic" refers to an aromatic group as defined above except that one or more ring carbon atoms is replaced by N, O or S.

The term "electron deficient" refers to an aromatic or heteroaromatic system which is substituted such that it has a deficiency of electrons in the π bond system when compared with an unsubstituted aromatic or heteroaromatic ring system.

It is well understood by skilled chemists that in order to carry out efficient nucleophilic substitution of aromatic ring systems, it is necessary to ensure that the aromatic ring system is electron deficient. This also applies to the method of the present invention and it is therefore essential that the aromatic or heteroaromatic ring system (Q in general formulae (I) and (II)) is electron deficient. A skilled chemist would easily be able to recognise which aromatic and heteroaromatic systems could be fluoridated by the method of the invention and which could not.

In line with this, $R^1$ to $R^5$ are chosen so that taken together the aromatic ring Q is more electron deficient than the substituted benzene ring ensuring that fluoridation occurs on ring Q and the iodonium salt is stable enough to be a useful precursor for the fluoridation of Q.

The most preferred $R^1$-$R^5$ groups of the invention are hydrogen, $C_{1-3}$ alkyl, —O—($C_1$-$C_3$ alkyl), particularly hydrogen, methyl and methoxy.

In the compound of Formula II, the "solid support" may be any suitable solid-phase support which is insoluble in any solvents to be used in the process but to which the linker can be covalently bound. Examples of suitable solid supports include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a reaction vessel, for example a cartridge or a microfabricated vessel. Carrying out the method of the invention on such a solid support enables the product of the fluoridation to be obtained in pure form without the need for any additional separation step. This is especially advantageous when the fluoridation is a radiofluoridation as any time saved in the method of preparation will result in a higher radiochemical yield.

In the compound of Formula II the "linker" may be any suitable organic group which serves to space the reactive site sufficiently from the solid support structure so as to maximise reactivity. Suitably, the linker comprises $C_{1-20}$ alkyl, $C_{1-20}$ alkoxy, attached to the resin by an amide ether or a sulphonamide bond for ease of synthesis The linker may also suitably be a polyethylene glycol (PEG) linker. Examples of such linkers are well known to those skilled in the art of solid-phase chemistry.

As already mentioned, it is essential that the group Q is electron deficient and therefore, if the aromatic ring system does have an electron donating substituent such as an OH or amino group, it must also contain one or more electron withdrawing groups. It is also preferred that if the group Q does contain an electron donating substituent, this is at the meta position with respect to the $I^+$ in general formulae (I) and (II).

Examples of suitable substituents for the group Q are $C_{1-10}$ alkyl, —O($C_{1-10}$ alkyl), —C(=O)$C_{1-10}$ alkyl, —C(=O)$NR^6$($C_{1-10}$ alkyl), —($C_1$-$C_6$ alkyl)—O—($C_1$-$C_6$ alkyl), $C_{5-14}$ aryl, —O($C_{5-14}$ aryl), —C(=O)$C_{5-14}$ aryl, —C(=O)$NR^6$($C_{5-14}$ aryl, $C_{5-14}$ heteroaryl, —O($C_{5-14}$ heteroaryl), —C(=O)$C_{5-14}$ heteroaryl, —C(=O)$NR^6$($C_{5-14}$ heteroaryl), $C_{3-10}$ cycloalkyl, —O($C_{3-10}$ cycloalkyl), —C(=O)($C_{3-10}$ cycloalkyl), —C(=O)$NR^6$($C_{3-10}$ cycloalkyl), $C_{3-10}$ heterocyclyl, —O($C_{3-10}$ heterocyclyl), —C(=O)($C_{3-10}$ heterocyclyl), —C(=O)$NR^6$($C_{5-14}$ heterocyclyl),
wherein $R^6$ is H, $C_1$-$C_6$ alkyl, $C_3$-$C_{10}$ cycloalkyl, $C_3$-$C_{10}$ heterocyclyl, $C_4$-$C_{10}$ aryl or $C_4$-$C_{10}$ heteroaryl;
any of which may optionally be substituted with OH, $NHR^6$, COOH or protected versions any of these groups; or alternatively
any two adjacent substituents may form a four- to six-membered carbocyclic or heterocyclic ring, optionally fused to a further aromatic, heteroaromatic, carbocyclic or heterocyclic ring.

The aromatic moiety Q may have other, electron donating substituents such as OH, $NHR^6$ or halogen only if there is also an electron withdrawing substituent present.

Especially preferred examples of Q are illustrated in Table I below.

TABLE I

Preferred compounds produced by the method of the invention

| $^{18}$F Compound | Precursor (Q) |
|---|---|
| (c) [$^{18}$F]-5-fluorouracil | |
| (d) [$^{18}$F]-mFBG | |
| (e) [$^{18}$F]-FIBG | |
| (f) [$^{18}$F]-fluorocarazolol | |
| (g) [$^{18}$F]-pmPPF | |
| (h) [$^{18}$F]-altanaserine | |

TABLE I-continued

Preferred compounds produced by the method of the invention

| $^{18}$F Compound | Precursor (Q) |
|---|---|
| (i) [$^{18}$F]-2-A85380 | |
| (j) [$^{18}$F]-SC58125 | |
| (k) [$^{18}$F]-Tyrosine | |
| (l) [$^{18}$F]-Spiro-FBT | |
| (m) [$^{18}$F]-FDP | |

TABLE I-continued

Preferred compounds produced by the method of the invention $^{18}$F Compound / Precursor (Q)

(n) [$^{18}$F]-flumanezil (o) [$^{18}$F]-SFB labelling agent (p)

Whether the method of the invention is carried out in solution or on a solid phase, the fluorine-labelled compound is preferably an [$^{18}$F]-labelled compound and the fluoride ion source is preferably a source of $^{18}$F$^-$. Most preferably, the [$^{18}$F]-labelled compound is an [$^{18}$F]-labelled radiotracer, i.e. an [$^{18}$F]-labelled compound that is suitable for the detection by PET imaging of particular biological targets within a subject.

The [$^{18}$F]-labelled tracer is preferably selected from the compounds listed in the first column of Table I. The respective precursors of these [$^{18}$F]-labelled tracers are given in the second column of Table I, wherein $P^1$-$P^4$ are each independently hydrogen or a protecting group. Protection is achieved using standard methods, as described in Protecting groups in organic synthesis, Theodora W. Greene and peter G. M. Wuts, Published by John Wiley & Sons Inc.

Where the method of the invention involves the preparation of an [$^{18}$F]-labelled compound, the method may further comprise one or more of the following steps in any order:
(i) removal of excess $^{18}$F$^-$, for example by ion-exchange chromatography; and/or
(ii) removal of the protecting groups; and/or
(iii) removal of organic solvent; and/or
(iv) formulation of the resultant compound as an aqueous solution.

The method of the present invention may be carried out using a kit and, therefore, in a second aspect, the present invention relates to a kit for the production of an aromatic fluorine-labelled compound according to the method of the first aspect of the invention, the kit comprising:
(i) a vial containing an aqueous solvent for dissolving the fluoride ion source; and
(ii) a reaction vessel containing an iodonium salt.

The iodonium salt may be a compound of general formula (I) or (II) defined above. When the iodonium salt is a compound of general formula (II), the solid support may comprise a coating on the surface of the reaction vessel.

Suitable reaction vessels comprise cartridges and microfabricated vessels, both of which are well known to those of skill in the art.

The kit may also comprise a source of fluoride ions which may be provided dissolved in the aqueous solvent in the vial or may alternatively be provided in a separate container.

Preferred solvents and sources of fluoride ions are as discussed above for the first aspect of the invention.

When the product of the method of the invention is a [$^{18}$F]-radiotracer or imaging agent, for example the compounds shown in column 1 of Table 1, it is useful in a method for obtaining an image of a patient, the method comprising administering to the patient an [$^{18}$F]-labelled imaging agent obtained by the method of the invention and obtaining an image of the patient by detecting the presence in the patient's body of the [$^{18}$F]-labelled imaging agent.

An [$^{18}$F]-imaging agent obtained by the method of the invention may be used in a pharmaceutical composition.

A "pharmaceutical composition" is defined in the present invention as a formulation comprising the imaging agent of the invention or a salt thereof in a form suitable for administration to humans. The pharmaceutical composition may be administered parenterally, i.e. by injection, and is most preferably an aqueous solution. Such a composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid).

EXAMPLES

A number of experiments were carried out to evaluate fluoridation of iodonium salts in the presence of water.

Comparative Example 1

Radiofluoridation of Diphenyliodonium Triflate with Potassium/Kryptofix Counterion

[$^{18}$F] Fluoride in $^{18}$O enriched water ((~0.3 ml) was loaded into a reaction vessel, to this was added kryptofix 222 (11.4 mg) and potassium carbonate (0.2 ml of a 0.1 M solution) in acetonitrile. The fluoride was dried by azeotropic drying. Following the completion of the drying process, a solution of diphenyliodonium triflate (ex Sigma-Aldrich Chemicals, 22.5 mg) in dry acetonitrile (1 ml) was added to the dry fluoride. The mixture was heated at 95° C. for 15 minutes before being cooled in a stream of compressed air. The product was transferred to a sealed collection vial and the reaction analysed by high-performance liquid chromatography (HPLC) over a Phenomenex Luna 3 micron C18 column (150×4.6 mm) using a 1 ml/min gradient elution from 5% to 95% 0.1% trifluoroacetic acid (TFA) in acetonitrile in 0.1% TFA in water over 15 minutes.

Example 2

Radiofluoridation of Diphenyliodonium Triflate in 9:1 Acetonitrile:Water with Potassium/Kryptofix Counterion

[$^{18}$F] Fluoride in $^{18}$O enriched water (~0.3 ml) was loaded into the reaction vessel, to this was added kryptofix 222 (11.4 mg) and potassium carbonate (0.2 ml of a 0.1 M solution) in acetonitrile. The fluoride was dried by azeotropic drying. Following the completion of the drying process, a solution of diphenyliodonium triflate (ex Sigma-Aldrich Chemicals, 23.0 mg) in a mixture of dry acetonitrile (0.9 ml) and water (0.1 ml) was added to the dry fluoride. The mixture was heated at 100° C. for 15 minutes before being cooled in a stream of compressed air. The product was transferred to a sealed collection vial and the reaction analysed by HPLC as described in Example 1.

Example 3

Radiofluoridation of Diphenyliodonium Triflate in 3:1 Acetonitrile:Water Using Undried Fluoride with Potassium/Kryptofix Counterion

[$^{18}$F] Fluoride in $^{18}$O enriched water (~0.1 ml) was loaded into the reaction vessel, to this was added kryptofix 222 (11.4 mg), potassium carbonate (0.2 ml of a 0.1 M solution) in acetonitrile (0.9 ml) and diphenyliodonium triflate (ex Sigma-Aldrich Chemicals, 21.7 mg). The mixture was heated at 100° C. for 15 minutes before being cooled in a stream of compressed air. The product was transferred to a sealed collection vial and the reaction analysed by HPLC as described in Example 1.

Example 4

Radiofluoridation of Diphenyliodonium Triflate in 3:1 Acetonitrile:Water Using Undried Fluoride with Potassium Counterion

[$^{18}$F] Fluoride in $^{18}$O enriched water (~0.1 ml) was loaded into the reaction vessel, to this was added potassium carbonate (0.2 ml of a 0.1 M solution) in acetonitrile (0.9 ml) and diphenyliodonium triflate (ex Sigma-Aldrich Chemicals, 23.2 mg). The mixture was heated at 100° C. for 15 minutes before being cooled in a stream of compressed air. The product was transferred to a sealed collection vial and the reaction analysed by HPLC as described in Example 1.

Example 5

Radiofluoridation of Diphenyliodonium Triflate in 9:1 Acetonitrile:Water with Potassium Carbonate Counterion

[$^{18}$F] Fluoride in $^{18}$O enriched water (~0.3 ml) was loaded into the reaction vessel, to this was added potassium carbonate (0.2 ml of a 0.1 M solution) in acetonitrile. The fluoride was dried by azeotropic drying. Following the completion of the drying process, a solution of diphenyliodonium triflate (ex Sigma-Aldrich Chemicals, 28.7 mg) in a mixture of dry acetonitrile (0.9 ml) and water (0.1 ml) was added to the dry fluoride. The mixture was heated at 100° C. for 15 minutes before being cooled in a stream of compressed air. The product was transferred to a sealed collection vial and the reaction analysed by HPLC as described in Example 1.

Comparative Example 6

Radiofluoridation of Diphenyliodonium Tetraphenylborate with Caesium Counterion

[$^{18}$F] Fluoride in $^{18}$O enriched water ((~0.3 ml) was loaded into the reaction vessel, to this was added caesium carbonate (24 mg), water (0.2 ml) and acetonitrile (1 ml). The fluoride was dried by azeotropic drying. Following the completion of the drying process, a solution of diphenyliodonium tetraphenylborate (ex Sigma-Aldrich Chemicals, 22.5 mg) in dry acetonitrile (1 ml) was added to the dry fluoride. The mixture was heated at 95° C. for 15 minutes before being cooled in a stream of compressed air. The product was transferred to a sealed collection vial and the reaction analysed by HPLC as described in Example 1.

Example 7

Radiofluoridation of Diphenyliodonium Triflate in 99:1 Acetonitrile:Water with Caesium Carbonate Counterion

[$^{18}$F] Fluoride in $^{18}$O enriched water (~0.3 ml) was loaded into the reaction vessel, to this was added caesium carbonate (27.7 mg), water (0.2 ml) and acetonitrile (1 ml). The fluoride was dried by azeotropic drying. Following the completion of the drying process, a solution of diphenyliodonium triflate (ex Sigma-Aldrich Chemicals, 24.8 mg) in a mixture of dry acetonitrile (0.99 ml) and water (0.01 ml) was added to the dry fluoride. The mixture was heated at 100° C. for 20 minutes before being cooled in a stream of compressed air. The product was transferred to a sealed collection vial and the reaction analysed by HPLC as described in Example 1.

Example 8

Radiofluoridation of Diphenyliodonium Tetraphenylborate in 9:1 Acetonitrile:Water with Caesium Carbonate Counterion

[$^{18}$F] Fluoride in $^{18}$O enriched water (~0.3 ml) was loaded into the reaction vessel, to this was added caesium carbonate (27.7 mg), water (0.2 ml) and acetonitrile (1 ml). The fluoride was dried by azeotropic drying. Following the completion of the drying process, a solution of diphenyliodonium triflate (ex Sigma-Aldrich Chemicals, 24.9 mg) in a mixture of dry acetonitrile (0.9 ml) and water (0.1 ml) was added to the dry fluoride. The mixture was heated at 100° C. for 20 minutes before being cooled in a stream of compressed air. The product was transferred to a sealed collection vial and the reaction analysed by HPLC as described in Example 1.

Example 9

Radiofluoridation of Diphenyliodonium Tetraphenylborate in 7:3 Acetonitrile:Water Using Undried Fluoride with Caesium Carbonate Counterion

[$^{18}$F] Fluoride in $^{18}$O enriched water (~0.6 ml) was loaded into the reaction vessel, to this was added caesium carbonate (~27 mg), acetonitrile (0.7 ml) and diphenyliodonium triflate (ex Sigma-Aldrich Chemicals, 26.5 mg). The mixture was heated at 100° C. for 15 minutes before being cooled in a stream of compressed air. The product was transferred to a sealed collection vial and the reaction analysed by HPLC as described in Example 1.

Example 10

Radiofluoridation of Diphenyliodonium Tetraphenylborate in 1:1 Acetonitrile:Water Using Undried Fluoride with Caesium Carbonate Counterion

[$^{18}$F] Fluoride in $^{18}$O enriched water (~0.3 ml) was loaded into the reaction vessel, to this was added caesium carbonate (~27 mg), acetonitrile (0.5 ml), water (0.2 ml) and diphenyliodonium triflate (ex Sigma-Aldrich Chemicals, 25.3 mg). The mixture was heated at 100° C. for 15 minutes before being cooled in a stream of compressed air. The product was transferred to a sealed collection vial and the reaction analysed by HPLC as described in Example 1.

The results obtained in Examples 1 to 10 are summarised in Table II below [RCP=radiochemical purity; yield is decay-corrected]:

TABLE II

Summary of Results from Examples 1 to 10

| Example | Fluoride counter-ion | % Water in reaction solvent | RCP % | Yield % |
|---|---|---|---|---|
| 1 (comparative)[1] | K$^+$/Kryptofix | 0 | 13 | 10 |
| 2 | K$^+$/Kryptofix | 10 | 90 | 52 |
| 3 | K$^+$/Kryptofix | 25 | 40 | 32 |
| 4 | K$^+$ | 25 | 42 | 30 |
| 5 | K$^+$ | 10 | 98 | 36 |
| 6 (comparative) | Cs$^+$ | 0 | 90 | 3 |
| 7 | Cs$^+$ | 1 | 90 | 15 |
| 8 | Cs$^+$ | 10 | 90 | 62 |
| 9 | Cs$^+$ | 30 | 78 | 73 |
| 10 | Cs$^+$ | 50 | 21 | 20 |

[1]These figures are an average over 21 experiments

Example 11

Preparation of 4-[$^{18}$F] Fluorophenyl Methyl Ketone

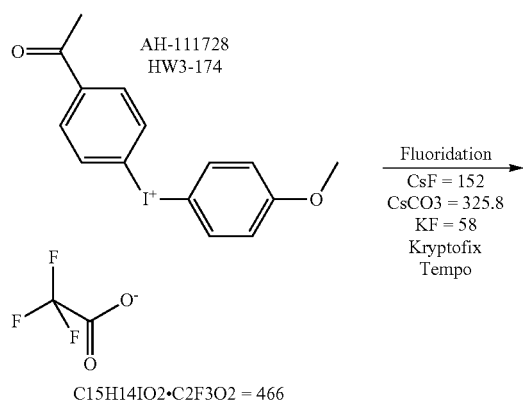

C15H14IO2·C2F3O2 = 466

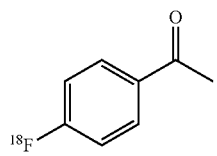

(4-carboxymethylphenyl), (4-methoxyphenyl) iodonium triflate was reacted with a source of fluoride ions in a solvent according the method set out in Examples 1 to 10. The results for various combinations of fluoride ion source and solvent are set out in Table III.

TABLE III

Results of Example 11

| Expt | Conditions | Radiochem. purity of product % | Recovery of activity from reaction vessel % | Overall yield RCP × Recovery |
|---|---|---|---|---|
| 11A | Caesium fluoride Carbonate Water/ acetonitrile10% 15 min 100° C. | 67 | 65 | 44 |
| Comparative 11B(i) | Potassium fluoride carbonate Kryptofix acetonitrile 15 min 100° C. | 30 | 40 | 12 |
| Comparative 11B(ii) | Potassium fluoride carbonate Kryptofix acetonitrile 15 min 100° C. | 26 | 57 | 15 |
| Comparative 11C | Potassium fluoride carbonate Kryptofix acetonitrile tempo 15 min 100° C. | 73 | 71 | 52 |
| 11D | Caesium fluoride Carbonate Water acetonitrile10% 30 min 120° C. | 94 | 64 | 60 |
| Comparative 11E | Potassium fluoride carbonate tempo Kryptofix acetonitrile 30 min 120° C. | 82 | 74 | 61 |

The results in Table III show that using the method of the invention, the overall yield of product is comparable with and, in many cases, greater than the overall yield obtained from the conventional processes used in the comparative examples.

Example 12

Preparation of 4-[$^{18}$F] fluoro-2-methoxy-5-methylphenyl methyl ketone

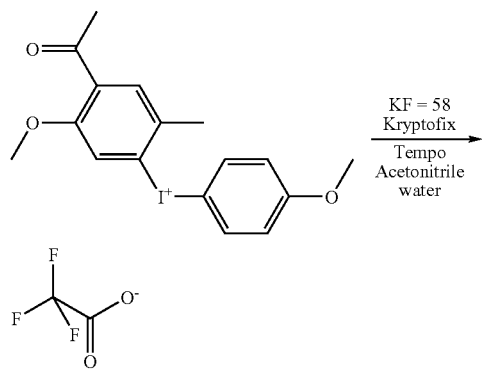

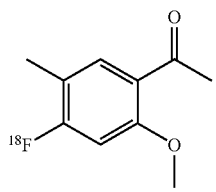

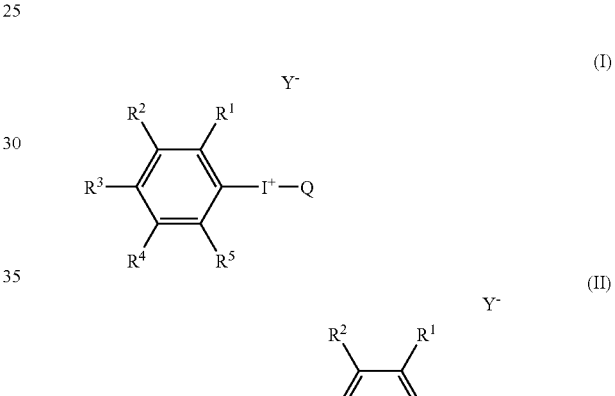

(4-carboxymethyl-3-methoxy-6-methylphenyl), (4-methoxyphenyl) iodonium triflate was reacted with a source of fluoride ions in a solvent according the method set out in Examples 1 to 10. The results for various combinations of fluoride ion source and solvent are set out in Table IV.

| Experiment | Conditions | Radiochem purity of product % | Recovery of activity from reaction vessel % | Overall yield RCP × Recovery |
|---|---|---|---|---|
| 12A(i) | Potassium fluoride and carbonate tempo 30 min 120° C. Kryptofix acetonitrile | 42 | 65 | 27% |
| 12A(ii) | Potassium fluoride and carbonate tempo 30 min 120° C. Kryptofix acetonitrile | 64 | 63 | 40 |
| 12A(iii) | Potassium fluoride and carbonate tempo 30 min 120° C. Kryptofix acetonitrile | 59 | 57 | 34 |
| | Average results | 55 | 62 | 34 |
| Comparative 12B(i) | Potassium fluoride and carbonate tempo 30 min 120° C. Kryptofix acetonitrile 15% water | 64 | 83 | 53 |
| Comparative 12B(ii) | Potassium fluoride and carbonate tempo 30 min 120° C. Kryptofix acetonitrile 15% water | 56 | 80 | 45 |
| | Average results | 60 | 81.5 | 49% |

The results presented in Table III demonstrate that the presence of water in the reaction improves the yield and that more complex molecules can be prepared equally effectively using the method of the invention.

The invention claimed is:

1. A method for the production of an aromatic or hetroaromatic fluorine-labelled compound comprising fluoridation of an iodonium salt of Formula (I) or (II):

wherein:
Q=phenyl, or phenyl substituted with one or more of acetyl, C1-3 alkyl or —O—C1-3 alkyl each of $R^1$-$R^5$ is independently selected from hydrogen, $C_{1-3}$ alkyl and —O—($C_1$-$C_3$ alkyl); and
$Y^-$ is a counter ion such as trifluoromethane sulfonate (triflate), perfluoro $C_2$-$C_{10}$ alkyl sulphonate, trifluoroacetate, methane sulfonate (mesylate), toluene sulfonate, (tosylate), tetraphenylborate;
to give a product of general formula (III):

Q-F        (III)

and wherein said fluoridation is carried out with a fluoride ion source characterised in that the reaction solvent is either 100% water or a mixture of water and a water miscible solvent.

2. A method as claimed in claim 1, wherein the water miscible solvent is acetonitrile, ethanol, methanol, tetrahydrofuran or dimethylformamide.

3. A method as claimed in claim 1 wherein the volume: volume ratio of water:water-miscible solvent is between 1:99 and 1:1.

4. A method as claimed in claim 3 wherein the volume: volume ratio of water:water-miscible solvent is from 10:90 to 30:70.

5. A method as claimed in claim 1, wherein the fluoride ion source is potassium, caesium or sodium fluoride.

6. A method as claimed in claim 1 wherein, in the compound of Formula II, the "solid support" is polystyrene, polyacrylamide, polypropylene or glass or silicon coated with such a polymer.

7. A method as claimed in claim 1 wherein the solid support is in the form of small discrete particles or is a coating on the inner surface of a reaction vessel.

8. A method as claimed in claim 1, wherein, in the compound of Formula II the "linker" is $C_{1-20}$ alkyl or $C_{1-20}$ alkoxy, attached to the resin by an amide ether or a sulphonamide bond or a polyethylene glycol (PEG) linker.

9. A method as claimed in claim 1 wherein $R^6$ is H, $C_1$-$C_6$ alkyl, $C_3$-$C_{10}$ cycloalkyl, $C_3$-$C_{10}$ heterocyclyl, $C_4$-$C_{10}$ aryl or $C_4$-$C_{10}$ heteroaryl;

any of which may optionally be substituted with OH, $NHR^6$, COOH or protected versions any of these groups; or alternatively any two adjacent substituents may form a four- to six-membered carbocyclic or heterocyclic ring, optionally fused to a further aromatic, heteroaromatic, carbocyclic or heterocyclic ring.

10. A method as claimed in claim 1, wherein the fluorine-labelled compound is an [$^{18}$F]-labelled compound and the fluoride ion source is a source of $^{18}F^-$.

11. A method as claimed in claim 1, further including, in any order, one or more of the following steps: removal of excess $^{18}F^-$, for example by ion-exchange chromatography; and/or
  (i) removal of the protecting groups; and/or
  (ii) removal of organic solvent; and/or
  (iii) formulation of the resultant compound as an aqueous solution.

12. A kit for the production of an aromatic fluorine-labelled compound, the kit comprising:
  (i) a vial containing an aqueous solvent for dissolving the fluoride ion source; and
  (ii) a reaction vessel containing an iodonium salt of claim 1.

13. A kit as claimed in claim 12, wherein the solvent is 100% water.

14. A kit as claimed in claim 12 wherein the solvent is a mixture of water and a water miscible solvent.

15. A kit as claimed in claim 14, wherein the water miscible solvent is acetonitrile, ethanol, methanol, tetrahydrofuran or dimethylformamide.

16. A kit as claimed in claim 14 wherein the volume: volume ratio of water:water-miscible solvent is between 1:99 and 1:1.

17. A kit as claimed in claim 16 wherein the volume: volume ratio of water:water-miscible solvent is from 10:90 to 30:70.

18. A kit as claimed in claim 12, wherein the reaction vessel is a cartridge or a microfabricated vessel.

19. A kit as claimed in claim 12, further comprising a source of fluoride ions.

* * * * *